(12) United States Patent
Fathi et al.

(10) Patent No.: US 6,707,018 B2
(45) Date of Patent: Mar. 16, 2004

(54) MICROWAVE THAWING PACKAGE AND METHOD

(75) Inventors: Zakaryae Fathi, Cary, NC (US); Robert J. Lauf, Oak Ridge, TN (US)

(73) Assignee: UT-Battelle, LLC, Knoxville, TN (US)

( * ) Notice: Subject to any disclaimer, the term of this patent is extended or adjusted under 35 U.S.C. 154(b) by 69 days.

(21) Appl. No.: 10/120,753

(22) Filed: Apr. 11, 2002

(65) Prior Publication Data

US 2003/0192883 A1 Oct. 16, 2003

(51) Int. Cl.[7] .................................................. H05B 6/80
(52) U.S. Cl. ........................................ 219/703; 219/729
(58) Field of Search ................................. 219/703, 729, 219/733, 704, 706, 709, 736, 756, 710, 728, 687, 697, 754, 762, 730; 374/149; 426/234, 107, 241; 588/11; 524/424

(56) References Cited

U.S. PATENT DOCUMENTS

| | | |
|---|---|---|
| 3,336,142 A | 8/1967 | Lawson |
| 3,505,490 A | 4/1970 | Gorn |
| 4,004,122 A | 1/1977 | Hallier |
| 4,233,325 A * | 11/1980 | Slangan et al. .............. 426/107 |
| 4,542,271 A * | 9/1985 | Tanonis et al. .............. 219/730 |
| 4,661,672 A * | 4/1987 | Nakanaga .................... 219/729 |
| 4,954,679 A | 9/1990 | Harms et al. |
| 5,003,142 A * | 3/1991 | Fuller ......................... 219/730 |
| 5,073,167 A | 12/1991 | Carr et al. |
| 5,118,747 A * | 6/1992 | Pollart et al. ............... 524/424 |
| 5,180,896 A | 1/1993 | Gibby et al. |
| 5,374,811 A | 12/1994 | Kiel et al. |
| 5,616,268 A | 4/1997 | Carr |
| 5,683,381 A | 11/1997 | Carr et al. |
| 5,690,614 A | 11/1997 | Carr et al. |
| 5,919,218 A | 7/1999 | Carr |
| 6,146,359 A | 11/2000 | Carr et al. |

* cited by examiner

Primary Examiner—Quang T. Van
(74) Attorney, Agent, or Firm—Joseph A. Marasco

(57) ABSTRACT

A package for containing frozen liquids during an electromagnetic thawing process includes: a first section adapted for containing a frozen material and exposing the frozen material to electromagnetic energy; a second section adapted for receiving thawed liquid material and shielding the thawed liquid material from further exposure to electromagnetic energy; and a fluid communication means for allowing fluid flow between the first section and the second section.

44 Claims, 6 Drawing Sheets

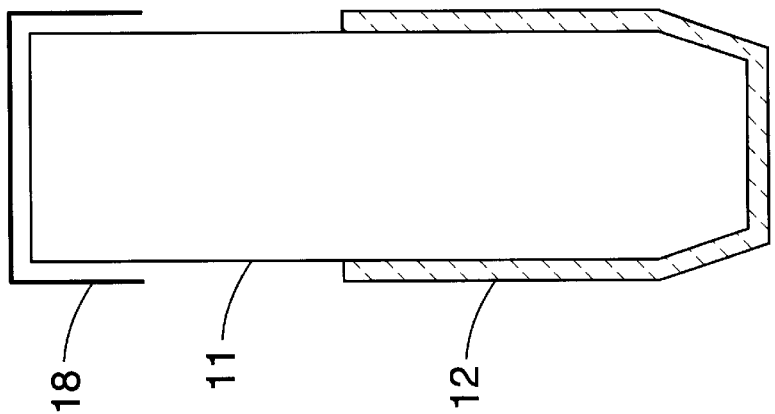
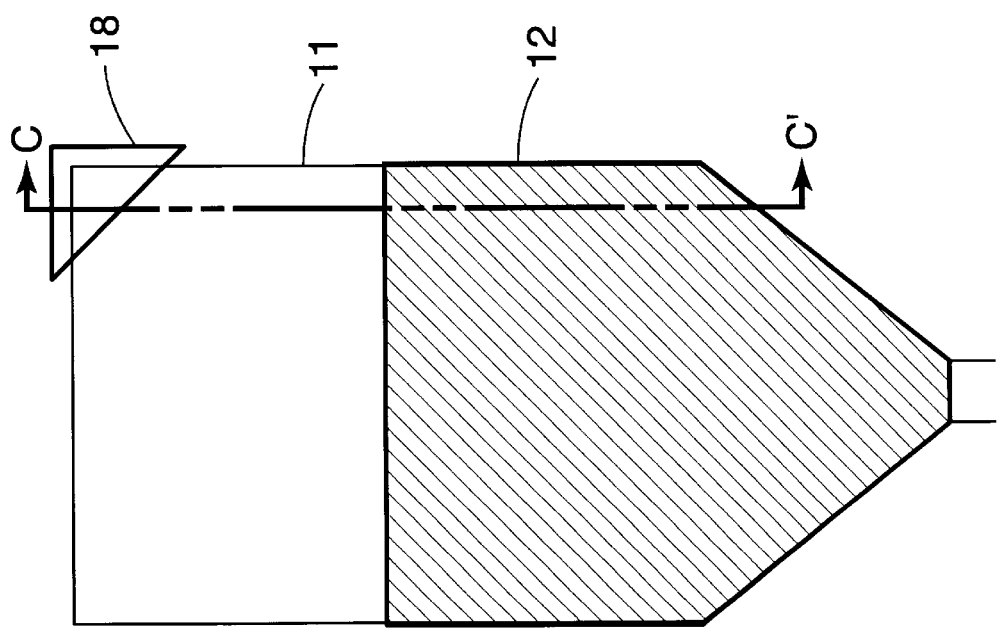

MICROWAVE THAWING PACKAGE AND METHOD

CROSS-REFERENCE TO RELATED APPLICATIONS

This application is related to another application filed on even date herewith and entitled "MICROWAVE THAWING APPARATUS AND METHOD", accorded U.S. patent application Ser. No. 10/120,860, the entire disclosure of which is incorporated herein by reference.

The United States Government has rights in this invention pursuant to contract no. DE-AC05-00OR22725 between the United States Department of Energy and UT-Battelle, LLC.

FIELD OF THE INVENTION

The present invention relates to devices and methods for thawing frozen materials by exposing same to electromagnetic energy, and more particularly to packaging systems and methods wherein thawed liquid is removed from exposure to the energy to prevent overheating the liquid.

BACKGROUND OF THE INVENTION

Many heat sensitive materials are frozen to prolong storage life. These include foodstuffs, pharmaceuticals, and particularly blood and blood products. It is often desirable to thaw these materials quickly, especially blood needed in emergency situations. At the same time, it is well known that it is very difficult to thaw frozen materials by microwave heating in a controlled and reproducible way, because the loss tangent of water is so much greater than that of ice. Once a small portion of the material is melted, that portion rapidly absorbs additional microwave energy and begins cooking.

In the field of microwave radiation, it is well known that microwave ovens may be constructed to operate at either fixed or variable frequency. Owing to the coupling ability of 2.45 GHz microwaves to water, this frequency is often used for cooking foods, drying, and other purposes wherein the principal material to be acted upon is water. However, it is well known that a multimode cavity operating at fixed frequency will display significant nonuniformities in the spatial power density owing to the formation of standing waves (or the excitation of only a small number of microwave modes within the cavity).

Recently, the use of frequency sweeping over a wide range as a means of mode stirring has been demonstrated and patented (Bible et al., U.S. Pat. No. 5,321,222). Modeling results and experimentation have shown that for typical multimode applicator cavities a bandwidth of about +/−5% of a center frequency provides a relatively uniform power density because of the superposition of many independent microwave modes (Bible et al. U.S. Pat. No. 5,961,871). Electronic frequency sweeping may be performed at a high rate of speed, thereby creating a much more uniform time-averaged power density throughout the furnace cavity. The desired frequency sweeping may be accomplished through the use of a variety of microwave electron devices. A helix traveling wave tube (TWT), for example, allows the sweeping to cover a broad bandwidth (e.g., 2 to 8 GHz) compared to devices such as the voltage tunable magnetron (2.45+0.05 GHz). Other devices such as klystrons and gyrotrons have other characteristic bandwidths, which may be suitable for some applications.

In fixed frequency ovens, attempts have been made at mode stirring, or randomly deflecting the microwave "beam", in order to break up the standing modes and thereby fill the cavity with the microwave radiation. One such attempt is the addition of rotating fan blades at the beam entrance of the cavity (Mizutani et al. U.S. Pat. No. 4,629,849). Alternatively, rotating feed horns (Kaneko et al. U.S. Pat. No. 4,176,266) and multiple feed horns (Jurgensen U.S. Pat. No. 3,916,137) have been described. None of these approaches creates a substantially uniform microwave power density within a "small" multimode cavity. Mechanical mode stirring devices do not in general provide enough of a physical perturbation and there is a limit to how fast they can be moved. Using multiple feeds becomes impractical when the number of feeds exceeds more than a few, and this is generally not adequate for true power uniformity within the cavity.

Another method used to overcome the adverse effects of standing waves is to intentionally create a standing wave within a single-mode cavity such that the workpiece may be placed at the location determined to have the highest power (the hot spot). Thus, only that portion of the cavity in which the standing wave is most concentrated will be used.

Other devices have been produced to change the parameters of the heating process of selected materials. Typical of the art are those devices disclosed in the following U.S. patents:

| Patent No. | Inventor(s) | Issue Date |
|---|---|---|
| 3,611,135 | D. L. Margerum | Oct. 5, 1971 |
| 3,916,137 | P. D. Jurgensen | Oct. 28, 1975 |
| 4,144,468 | G. Mourier | Mar. 13, 1979 |
| 4,176,266 | Y. Kaneko et al. | Nov. 27, 1979 |
| 4,196,332 | A. MacKay B, et al. | Apr. 1, 1980 |
| 4,340,796 | M. Yamaguchi, et al. | Jul. 20, 1982 |
| 4,415,789 | T. Nobue, et al. | Nov. 15, 1983 |
| 4,504,718 | H. Okatsuka, et al. | Mar. 12, 1985 |
| 4,593,167 | O. K. Nilssen | Jun. 3, 1986 |
| 4,629,849 | I. Mizutani et al. | Dec. 16, 1986 |
| 4,777,336 | J. Asmussen | Oct. 11, 1988 |
| 4,825,028 | P. H. Smith | Apr. 25, 1988 |
| 4,843,202 | P. H. Smith, et al. | Jun. 27, 1989 |
| 4,866,344 | R. I. Ross, et al. | Sep. 13, 1989 |
| 4,939,331 | B. Berggren, et al. | Jul. 3, 1990 |
| 5,321,222 | D. W Bible et al. | Jun. 14, 1994 |
| 5,700,326 | Takatsu et al. | Dec. 23, 1997 |
| 5,961,871 | D. W Bible et al. | Oct. 5, 1999 |

As previously mentioned, Bible et al. have described how frequency sweeping over a selected bandwidth, typically 5%, could establish a substantially uniform microwave power distribution within the cavity by the superposition of many hundreds of microwave modes. Nevertheless, none of the aforementioned approaches can completely address the fundamental difficulty of microwave thawing, namely, the large difference in dielectric loss between water and ice. The large increase in loss tangent upon melting creates an inherently unstable heating process in which the first volume of material to melt begins to absorb power selectively, rapidly leading to localized thermal runaway.

OBJECTS OF THE INVENTION

Accordingly, it is therefore an object of this invention to provide a microwave or other electromagnetic energy heating package in which a frozen material may be subjected to a controlled application of the energy.

It is another object of the present invention to provide a microwave or other electromagnetic energy heating package in which one may control the absorption of the energy within a frozen material to selectively begin melting the material at predetermined areas.

It is another object of the present invention to provide a microwave or other electromagnetic energy heating package in which one may protect already-melted liquid from further exposure to the energy by providing a shielded region for the thawed liquid.

It is a further object of the present invention to provide a microwave or other electromagnetic energy heating package in which one can manage the flow of liquid after melting to prevent the entrapment of liquid in areas that are exposed to the energy.

It is yet another object of the present invention to provide a method of applying a controlled concentration of microwave or other electromagnetic energy energy to a container of frozen material.

It is another object of the present invention to provide a method of controlling the absorption of microwave or other electromagnetic energy energy within a frozen material to selectively begin melting the material at predetermined areas.

Yet another object of the present invention is to provide a method of microwave or other electromagnetic energy thawing in which already-melted liquid is protected from further exposure to the energy.

It is a further object of the present invention to provide a method for microwave or other electromagnetic energy thawing in which the flow of liquid after melting is controlled to prevent the entrapment of liquid in areas that are exposed to the energy.

Further and other objects of the present invention will become apparent from the description contained herein.

SUMMARY OF THE INVENTION

In accordance with one aspect of the present invention, the foregoing and other objects are achieved by a package for containing frozen liquids during an electromagnetic thawing process which includes: a first section adapted for containing a frozen material and exposing the frozen material to electromagnetic energy; a second section adapted for receiving thawed liquid material and shielding the thawed liquid material from further exposure to electromagnetic energy; and a fluid communication means for allowing fluid flow between the first section and the second section.

In accordance with another aspect of the present invention, a package for containing frozen liquids during a microwave thawing process includes: a first section adapted for containing a frozen material and exposing the frozen material to electromagnetic energy, the first section including a lossy material for enhancing the thawing process; a second section adapted for receiving thawed liquid material; and a fluid communication means for allowing fluid flow between the first section and the second section.

In accordance with a further aspect of the present invention, a method of thawing a selected material includes the steps of: providing a package for containing frozen liquids during an electromagnetic thawing process comprising: a first section adapted for containing a frozen material and exposing the frozen material to electromagnetic energy; a second section adapted for receiving thawed liquid material and shielding the thawed liquid material from further exposure to electromagnetic energy; and a fluid communication means for allowing fluid flow between the first section and the second section; placing a material to be thawed into the first section; and exposing the first section to electromagnetic energy to thaw the material so that thawed liquid flows from the first section into the second section.

In accordance with another aspect of the present invention, a method of thawing a selected material includes the steps of: providing a package for containing frozen liquids during an electromagnetic thawing process comprising: a first section adapted for containing a frozen material and exposing the frozen material to electromagnetic energy, the first section including a lossy material for enhancing the thawing process; a second section adapted for receiving thawed liquid material; and a fluid communication means for allowing fluid flow between the first section and the second section; placing a material to be thawed into the first section; and exposing the first section to electromagnetic energy to thaw the material so that thawed liquid flows from the first section into the second section.

BRIEF DESCRIPTION OF THE DRAWINGS

FIG. 9 is a schematic front view of a microwave heating section of an embodiment of the present invention showing a lossy layer and a microwave-reflecting device.

FIG. 10 is a schematic cross-sectional side view through section C–C' of FIG. 9.

Like reference numerals are used for like elements in the drawings.

For a better understanding of the present invention, together with other and further objects, advantages and capabilities thereof, reference is made to the following disclosure and appended claims in connection with the above-described drawings.

DETAILED DESCRIPTION OF THE INVENTION

The present invention is designed to provide packages and methods for controlled microwave thawing of frozen materials while preventing thermal runaway in already-melted material. Some applicable processes include thawing of foodstuffs, pharmaceuticals, blood and blood products, biological tissue, other biological and/or chemical materials. Electromagnetic energy includes microwave, radio-frequency (RF), and infra-red (IR) types of energy.

Figure 2:
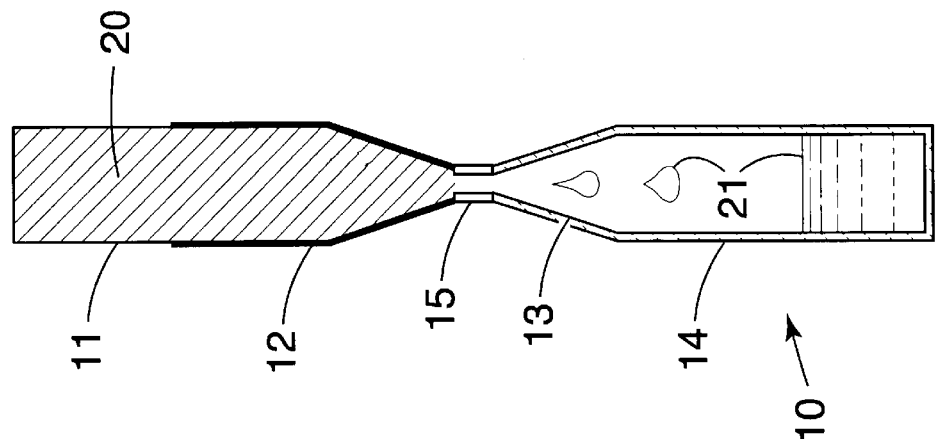
FIG. 2 is a schematic cross-sectional side view through section A–A' of FIG. 1.
Figure 1:
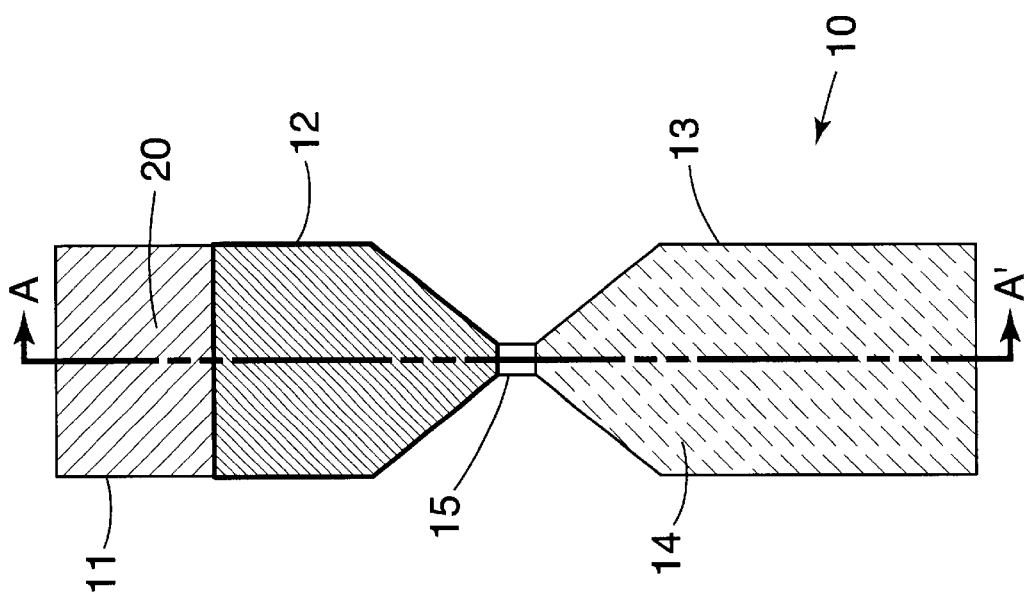
FIG. 1 is a schematic front view of an embodiment of the present invention wherein an upper section accommodates microwave heating while a lower, shielded section protects thawed liquid from further heating.

Referring to FIGS. 1 and 2, a package 10 in accordance with an embodiment of the present invention generally comprises three basic features, which are described as follows. A first section 11 is adapted for containing solid (frozen) material 20, and is also adapted for exposure to electromagnetic energy in order to thaw (melt) the solid material 20. A second section 13 is adapted for receiving thawed material 21.

A fluid communication means, or port 15 provides fluid communication between the first section 11 and the second section 13. The port 15 can be comprised of a constriction in the package 10, a coupling between discrete sections 11, 13, as shown in FIGS. 1 and 2, or other analogous structure. As solid material 20 contained in the first section 11 thaws and becomes liquid 21, it flows through the port 15 and into the second section 13, where the liquid 21 is shielded from further exposure to microwave energy by at least one of various means. The port 15 should be large enough to allow uninhibited flow of thawed liquid 21 therethrough, but small enough to so that significant lumps of solid material 20 cannot pass therethrough. The port 15 may include a suitable screen (not illustrated) for preventing unthawed material 20 from passing therethrough.

The first and second sections 11, 13 can be comprised of conventional or modified polymer bags, for example, blood bags, having openings that are interconnected by a polymer, metal, or ceramic coupling that serves as the port 15. The first section 11, and in some cases, the second section 13 also, should be constructed of "microwave safe" material. The first section can be constructed of an elastic material that can be expanded when filled with material 20, and which collapses to force liquid through the port 15 and into the second section 13.

As shown in FIGS. 1 and 2, the second section 13 may optionally include a microwave shielding material 14 that shields the liquid 21 from further exposure to microwave energy. Embodiments of the invention having a second section 13 that is coated or covered with a microwave shielding material 14 can be used in conventional and other microwave applicators that do not include means for shielding the liquid 21.

The microwave shielding material 14 can be comprised of any microwave reflecting material, for example, a metallic material or conductive cloth. The microwave shielding material 14 can be integral with the material of the second section 13, or it may be applied thereto in any form, for example, thick film coating, thin film coating, slip-cover, overlay, sleeve, etc. Coatings may be applied by any conventional process, for example, electrospray, vapor deposition, screen-printing, and the like.

Moreover, the microwave shielding material 14 can be comprised of a discrete (separate), even reusable component, such as a sheet or a sleeve, which can be slid over the second section 13 and which can be held in place by conventional fastening means, for example, tie, elastic band, clip, snap, hook, and the like. Aluminum metallization of the second section 13 or use of a reusable aluminum sleeve is quite suitable for most applications.

Moreover, the second section 13 may be optionally uncoated so that the package does not contribute to shielding the thawed liquid 21 from further exposure to microwave energy. Such embodiments of the present invention rely on features of the microwave applicator to shield the thawed liquid 21 from further exposure to microwave energy. See, for example, apparatus and methods described in the copending patent application cross-referenced and incorporated hereinabove.

The invention as illustrated in FIGS. 1 and 2 is applicable as shown to any thawing situation in which the liquid phase has substantially greater dielectric loss than the solid phase. For cases in which the density of the liquid phase is less than that of the solid phase (many polymers, for example) it will be appreciated that the package 10 shown in all the Figs., and particularly FIGS. 1 and 2 should be essentially inverted. The port 15 may include a check-valve (not illustrated) for preventing gravitational backflow of liquid 21 into the first section 11.

As shown in FIGS. 1 and 2, the first section 11 may optionally include a lossy material 12 or any other structure that enhances the thawing of the frozen material 20. The lossy material should also enhance the flow of liquid 21 to the port 15.

The lossy material 12 can be comprised of any material that absorbs energy at the particular frequency(s) used to carry out the thawing process, for example, ceramic and carbonaceous polymeric materials. "Lossy" is a general and well known term, but selection of a suitable lossy material 12 is dependent on several factors, including:

1. The particular type and frequency(s) of electromagnetic energy used to carry out the thawing process;
2. Characteristics of the particular material undergoing the thawing process, particularly the solid and liquid phases; and
3. Compatibility with the chemical and physical characteristics of the material that comprises the first section 13 of the package 10.

The lossy material 12 can be integral with the material of the first section 13, and/or the port 15. Alternatively, the lossy material 12 may be applied thereto in any form, for example, a thick or thin film coating, and by any conventional process, for example, electrospray, vapor deposition, screen printing, and the like. Dielectric carbonaceous materials are particularly useful for microwave thawing, for example, carbon black—polymer composites.

Figure 3:
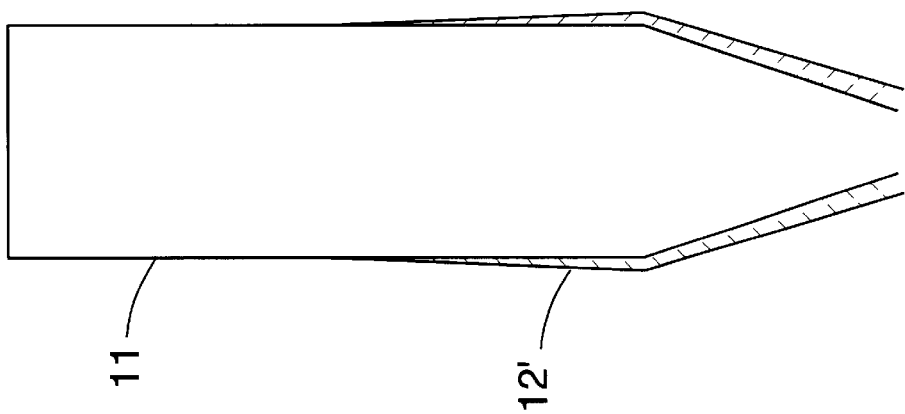
FIG. 3 is a schematic cross-sectional side view of a microwave heating section of an embodiment of the present invention showing a lossy (microwave-absorbing) layer having an essentially uniform thickness.
Figure 4:
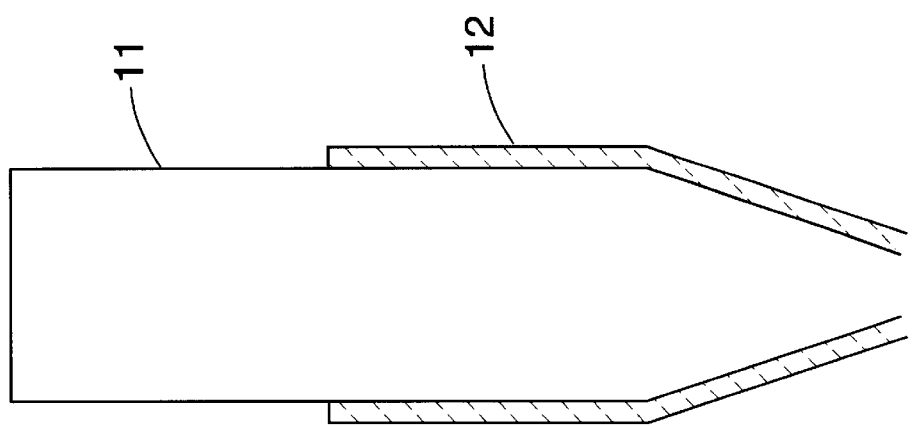
FIG. 4 is a schematic cross-sectional side view of a microwave heating section of an embodiment of the present invention showing a lossy layer having a tapered thickness.

Various configurations and modifications of lossy material are possible in sundry embodiments of the present invention. For example, FIG. 3 shows showing a layer of lossy material 12 having an essentially uniform thickness, which is contemplated to be most suitable for ease of manufacture. FIG. 4 shows showing a layer of lossy material 12' having a tapered thickness, which introduces a modest complexity to the manufacturing process, but would produce more heat near the port 15, where clogs would be most deleterious to liquid flow.

Figure 6:
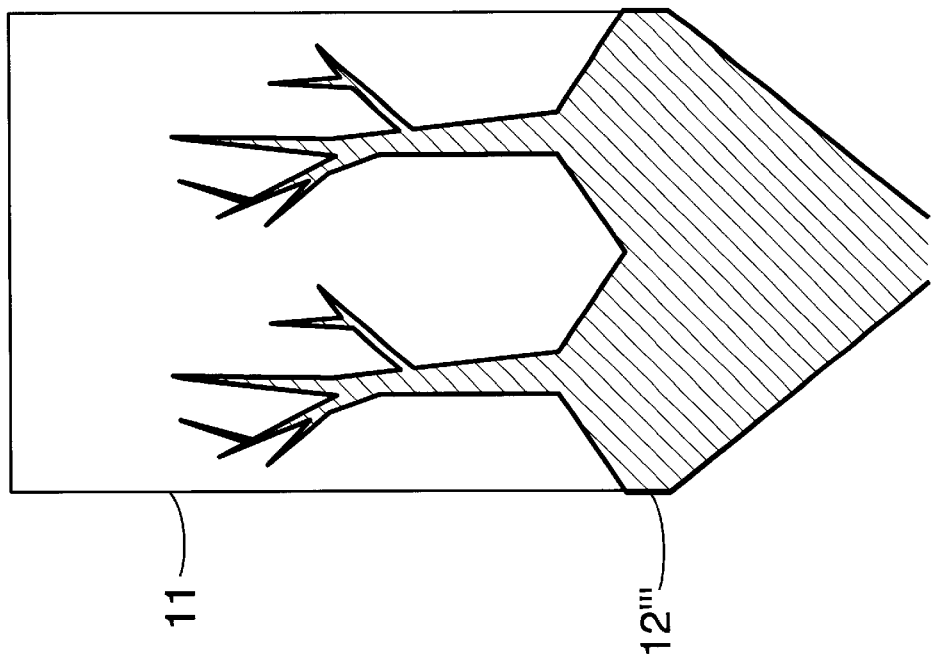
FIG. 6 is a schematic front view of a microwave heating section of an embodiment of the present invention showing a lossy layer having a branched configuration.
Figure 5:
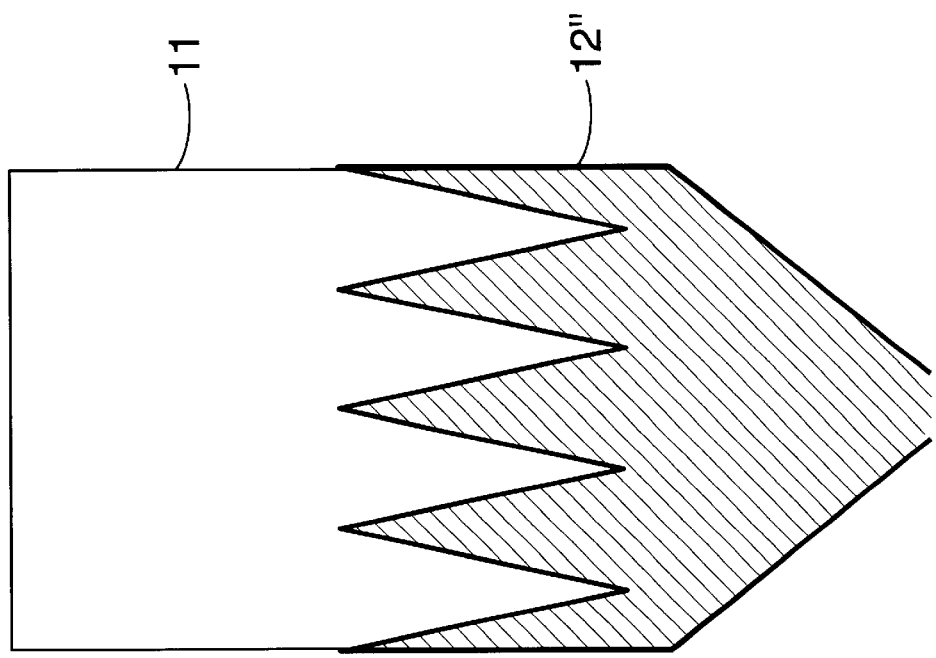
FIG. 5 is a schematic front view of a microwave heating section of an embodiment of the present invention showing a lossy layer having a saw-toothed configuration.

Moreover, FIG. 5 shows a lossy layer 12" having a saw-toothed configuration, and FIG. 6 shows a lossy layer 12'" having a branched configuration. These configurations promote rapid flow of liquid 21 to the second section 13 as shown in FIG. 1.

Figure 8:
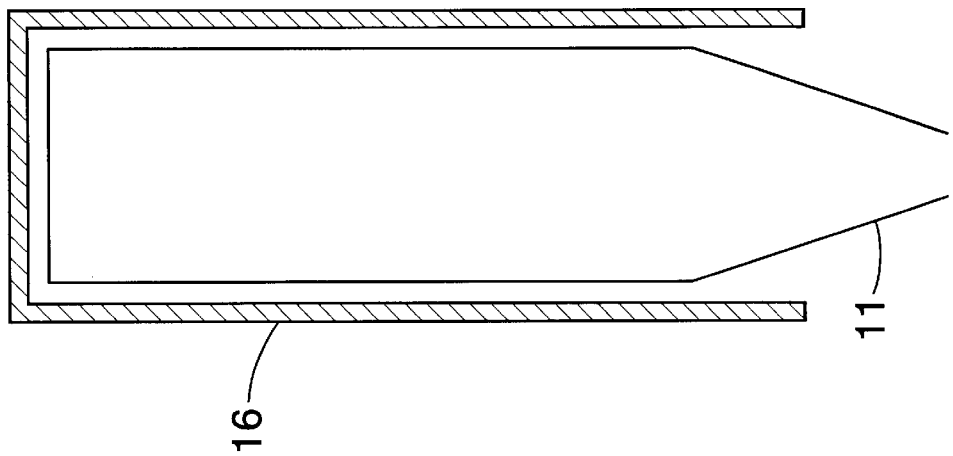
FIG. 8 is a schematic cross-sectional side view through section B–B' of FIG. 7.
Figure 7:
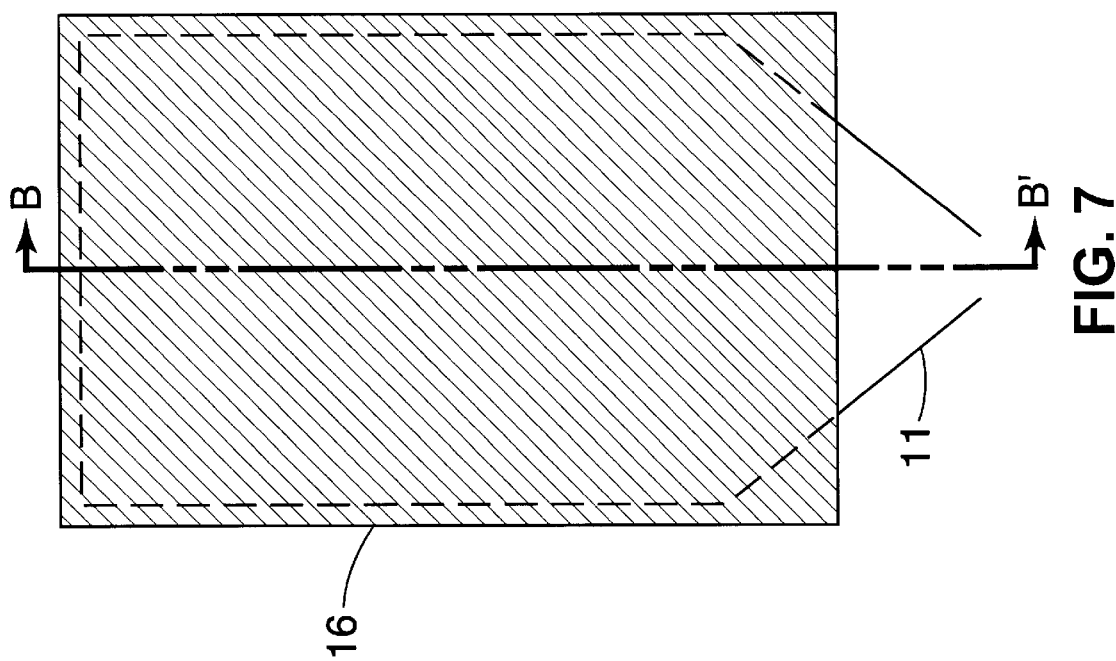
FIG. 7 is a schematic front view of a microwave heating section of an embodiment of the present invention showing a removable lossy overlay.

In another embodiment of the invention, as shown in FIGS. 7 and 8, the microwave lossy material 16 can be comprised of a discrete (separate), even reusable material, such as a sheet or a sleeve, which can be slid over the first section 13 and which can be held in place by conventional fastening means, for example, tie, elastic band, clip, snap, hook, and the like.

In addition to providing supplemental heating in selected areas of the first section 11, it is contemplated that it will be advantageous in some situations to provide some degree of microwave reflecting and/or shielding in some part of the first section 11 using, for example, an auxiliary component 18 such as a metallized area as shown in FIGS. 9 and 10. As discussed hereinabove, the auxiliary component 18 may be an integral, metallized layer created on the first section 11 during manufacture or it may be a separate reusable component.

Figure 11:
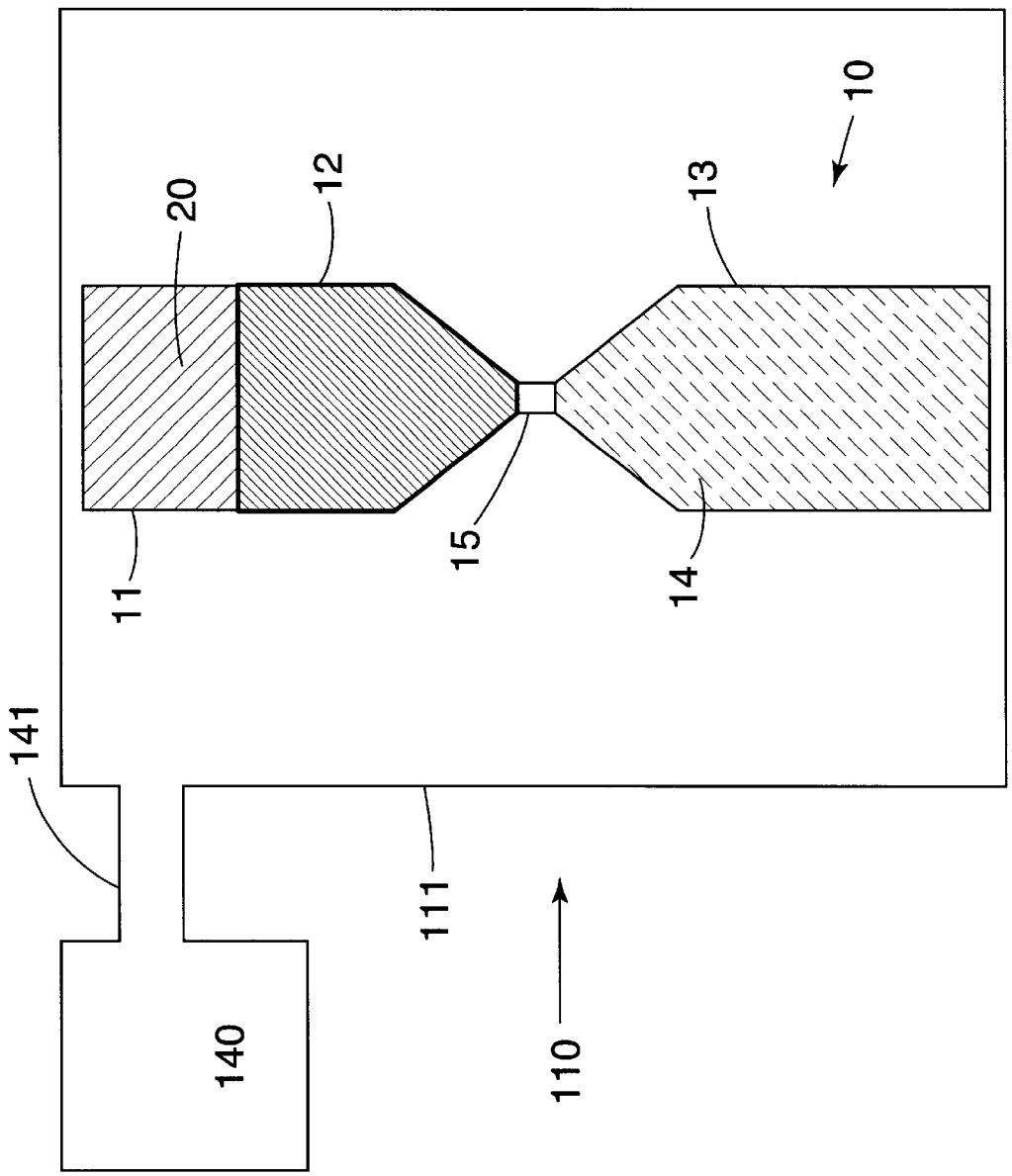
FIG. 11 is a schematic view showing an embodiment of the invention inside a microwave applicator.

FIG. 11 shows the embodiment of the invention as described hereinabove and shown in FIG. 1 inside a conventional microwave applicator 110. The microwave applicator 110 comprises a microwave applicator cavity 111 and a microwave source 140, which provides microwave energy to the microwave applicator cavity 111 through a waveguide 141.

EXAMPLE I

A VariWave™ 1500 variable frequency microwave oven (Lambda Technologies, Inc., Morrisville, N.C.) has a cavity 10"H×10"L×8"D and an operating frequency range of 6.5 to 18 GHz was used to test the present invention. The sample to be melted comprised a polymer bag containing 50 g of a frozen electrolyte solution that simulates the dielectric properties of human blood. With an applied power of approximately 120 W and heating for 50 s, the solution partially thawed, accompanied by overheating of thawed liquid to the point of cooking.

EXAMPLE II

In a system similar to that in the preceding example, a package as described hereinabove was employed. A sealed, two-section package contained the frozen solution in the upper, first section, and the lower, second section was completely wrapped with conductive cloth to shield the second section from microwave energy. The conductive cloth used was a polypyrrole treated 100% nylon impression fabric having a nominal resistance of 160 ohm/square range. The cloth was obtained from Milliken Research Corporation located in Spartanburg, S.C. (Contex Fabric).

Using this package, all of the frozen solution in the upper section was successfully thawed while the thawed, liquid solution flowed into the section and was thereby protected from further heating.

EXAMPLE III

In a system similar to that in the preceding example, a package was used that had a thick-film coating of carbon black-polymer composite on the upper section as described hereinabove. Using this package, all of the frozen solution in the upper section was successfully thawed while the thawed, liquid solution flowed more rapidly into the section and was thereby protected from further heating.

It will be seen from the foregoing that the packages and methods of the present invention offer convenient means for preventing thermal runaway during microwave heating operations in which the liquid phase has greater dielectric loss than the solid phase. It will be understood that the terms "melting" and "thawing" as used herein are interchangeable and that the materials to be melted or thawed may be pure materials, solutions, or mixtures and may have a melting temperature above, at, or below ambient. The solutions may be aqueous, nonaqueous, or polymer based.

It will be further understood that any other electromagnetic energy is applicable to the above description of the invention, for example, RF and IR.

While there has been shown and described what are at present considered the preferred embodiments of the invention, it will be obvious to those skilled in the art that various changes and modifications can be prepared therein without departing from the scope of the inventions defined by the appended claims.

What is claimed is:

1. A package for containing frozen liquids during an electromagnetic thawing process comprising:
    a first section adapted for containing a frozen material and exposing the frozen material to electromagnetic energy,
    a second section adapted for receiving thawed liquid material and shielding the thawed liquid material from further exposure to electromagnetic energy;
    a fluid communication means for allowing fluid flow between said first section and said second section; and,
    a clog preventing means for preventing clogging of said fluid communication means.

2. A package in accordance with claim 1 wherein said second section further comprises a coating of shielding material.

3. A package in accordance with claim 2 wherein said coating further comprises aluminum.

4. A package in accordance with claim 1 wherein said second section further comprises a discrete component of shielding material.

5. A package in accordance with claim 4 wherein said component further comprises aluminum.

6. A package in accordance with claim 1 wherein said second section further comprises an integral shielding material.

7. A package in accordance with claim 6 wherein said integral shielding material further comprises aluminum.

8. A package in accordance with claim 1 wherein said first section further comprises a coating of lossy material for enhancing the thawing process.

9. A package in accordance with claim 8 wherein said coating further comprises carbon.

10. A package in accordance with claim 1 wherein said first section further comprises a discrete component of lossy material for enhancing the thawing process.

11. A package in accordance with claim 10 wherein said component further comprises carbon.

12. A package in accordance with claim 1 wherein said first section further comprises an integral lossy material for enhancing the thawing process.

13. A package in accordance with claim 12 wherein said integral lossy material further comprises carbon.

14. A package in accordance with claim 1 wherein said first section and said second section further comprise polymer bags having openings and wherein said fluid communication means further comprises a coupling which interconnects said openings.

15. A package for containing frozen liquids during a microwave thawing process comprising:
    a first section adapted for containing a frozen material and exposing the frozen material to electromagnetic energy, said first section including a lossy material for enhancing the thawing process;
    a second section adapted for receiving thawed liquid material;
    a fluid communication means for allowing fluid flow between said first section and said second section; and,
    a clog preventing means for preventing clogging of said fluid communication means.

16. A package in accordance with claim 8 wherein said lossy material further comprises a coating.

17. A package in accordance with claim 16 wherein said coating further comprises carbon.

18. A package in accordance with claim 15 wherein said lossy material further comprises a discrete component.

19. A package in accordance with claim 18 wherein said component further comprises carbon.

20. A package in accordance with claim 15 wherein said lossy material further comprises a material that is integral with said first section.

21. A package in accordance with claim 20 wherein said first section further comprises carbon.

22. A package in accordance with claim 15 wherein said first section and said second section further comprise polymer bags having openings and wherein said fluid communication means further comprises a coupling which interconnects said openings.

23. A method of thawing a selected material comprising the steps of:
   a. providing a package for containing frozen liquids during an electromagnetic thawing process comprising: a first section adapted for containing a frozen material and exposing the frozen material to electromagnetic energy; a second section adapted for receiving thawed liquid material and shielding the thawed liquid material from further exposure to electromagnetic energy; a fluid communication means for allowing fluid flow between said first section and said second section; and a means for preventing clogging of said fluid communication means;
   b. placing a material to be thawed into said first section; and
   c. exposing said first section to electromagnetic energy to thaw said material so that thawed liquid flows from said first section into said second section.

24. A method in accordance with claim 23 wherein said second section further comprises a coating of shielding material.

25. A method in accordance with claim 24 wherein said coating further comprises aluminum.

26. A method in accordance with claim 23 wherein said second section further comprises a discrete component of shielding material.

27. A method in accordance with claim 26 wherein said component further comprises aluminum.

28. A method in accordance with claim 23 wherein said second section further comprises an integral shielding material.

29. A method in accordance with claim 28 wherein said integral shielding material further comprises aluminum.

30. A method in accordance with claim 23 wherein said first section further comprises a coating of lossy material for enhancing the thawing process.

31. A method in accordance with claim 30 wherein said coating further comprises carbon.

32. A method in accordance with claim 23 wherein said first section further comprises a discrete component of lossy material for enhancing the thawing process.

33. A method in accordance with claim 32 wherein said component further comprises carbon.

34. A method in accordance with claim 23 wherein said first section further comprises an integral lossy material for enhancing the thawing process.

35. A method in accordance with claim 34 wherein said integral lossy material further comprises carbon.

36. A method in accordance with claim 23 wherein said first section and said second section further comprise polymer bags having openings and wherein said fluid communication means further comprises a coupling which interconnects said openings.

37. A method of thawing a selected material comprising the steps of:
   a. providing a package for containing frozen liquids during an electromagnetic thawing process comprising: a first section adapted for containing a frozen material and exposing the frozen material to electromagnetic energy, said first section including a lossy material for enhancing the thawing process; a second section adapted for receiving thawed liquid material; a fluid communication means for allowing fluid flow between said first section and said second section; and a means for preventing clogging of said fluid communication means;
   b. placing a material to be thawed into said first section; and
   c. exposing said first section to electromagnetic energy to thaw said material so that thawed liquid flows from said first section into said second section.

38. A method in accordance with claim 37 wherein said lossy material further comprises coating.

39. A method in accordance with claim 38 wherein said coating further comprises carbon.

40. A method in accordance with claim 37 wherein said lossy material further comprises a discrete component.

41. A method in accordance with claim 40 wherein said component further comprises carbon.

42. A method in accordance with claim 37 wherein said lossy material further comprises a material that is integral with said first section.

43. A method in accordance with claim 42 wherein said first section further comprises carbon.

44. A method in accordance with claim 37 wherein said first section and said second section further comprise polymer bags having openings and wherein said fluid communication means further comprises a coupling which interconnects said openings.

* * * * *